(12) United States Patent
Fening et al.

(10) Patent No.: US 9,011,536 B2
(45) Date of Patent: Apr. 21, 2015

(54) APPARATUS AND METHOD FOR SEQUENTIALLY ANCHORING MULTIPLE GRAFT LIGAMENTS IN A BONE TUNNEL

(71) Applicant: The Cleveland Clinic Foundation, Cleveland, OH (US)

(72) Inventors: Stephen D. Fening, Willoughby Hills, OH (US); Anthony Miniaci, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 8 days.

(21) Appl. No.: 13/912,240

(22) Filed: Jun. 7, 2013

(65) Prior Publication Data

US 2013/0297021 A1    Nov. 7, 2013

Related U.S. Application Data

(63) Continuation of application No. 12/765,444, filed on Apr. 22, 2010, now Pat. No. 8,491,652.

(60) Provisional application No. 61/171,518, filed on Apr. 22, 2009.

(51) Int. Cl.
*A61F 2/08*     (2006.01)
*F16B 13/04*    (2006.01)
(Continued)

(52) U.S. Cl.
CPC ....... *A61F 2/0811* (2013.01); *A61B 2017/0425* (2013.01); *A61B 2017/0438* (2013.01);
(Continued)

(58) Field of Classification Search
USPC ....................................... 623/13.14
See application file for complete search history.

(56) References Cited

U.S. PATENT DOCUMENTS 5,356,435 A    10/1994    Thein
5,702,397 A    12/1997    Goble et al.
(Continued)

FOREIGN PATENT DOCUMENTS

EP    0232049 B1    1/1987
EP    0528573 A1    3/1992
(Continued)

OTHER PUBLICATIONS

Bergfeld et al., "Single- or Double- Bundle ACL Reconstruction: Technique vs. Concept", Orthopedics Today 2008, pp. 28-46.
(Continued)

*Primary Examiner* — Jacqueline Woznicki
(74) *Attorney, Agent, or Firm* — Tarolli, Sundheim, Covell & Tummino LLP

(57) ABSTRACT

An apparatus for anchoring at least two graft ligaments within a longitudinal bone tunnel includes a longitudinal sleeve having at least two ligament-contacting surfaces located in lateral opposition to a sleeve inner lumen. The sleeve is configured for at least partial insertion into the bone tunnel with each graft ligament positioned laterally adjacent a different ligament-contacting surface and at least partially located between the bone tunnel and the sleeve. An actuating member has proximal and distal actuating member ends. An asymmetrically offset profile is defined by the sleeve and/or the actuating member. The asymmetrically offset profile has engagement thresholds. The actuating member is inserted into the sleeve to cause frictional engagement of each graft ligament with both the bone tunnel and at least one ligament-contacting surface, the frictional engagement of each graft ligament being temporally spaced apart from the frictional engagement of at least one other graft ligament.

14 Claims, 4 Drawing Sheets

(51) Int. Cl.
  *E05C 5/04* (2006.01)
  *F16B 13/06* (2006.01)
  *F16B 13/12* (2006.01)
  *A61B 17/04* (2006.01)

(52) U.S. Cl.
  CPC . *A61F2002/0835* (2013.01); *A61F 2002/0852* (2013.01); *A61F 2002/0858* (2013.01); *A61F 2002/0882* (2013.01)

(56) References Cited

U.S. PATENT DOCUMENTS

| | | | |
|---|---|---|---|
| 5,916,216 A | 6/1999 | DeSatnick et al. | |
| 6,186,716 B1 * | 2/2001 | West et al. | 411/30 |
| 6,562,071 B2 | 5/2003 | Järvinen | |
| 6,632,245 B2 | 10/2003 | Kim | |
| 7,008,451 B2 | 3/2006 | Justin et al. | |
| 7,201,773 B2 | 4/2007 | Steiner et al. | |
| 7,235,074 B1 | 6/2007 | Sklar | |
| 7,326,247 B2 | 2/2008 | Schmieding et al. | |
| 7,329,281 B2 | 2/2008 | Hays et al. | |
| 2003/0144735 A1 | 7/2003 | Sklar et al. | |
| 2007/0156154 A1 | 7/2007 | Schlienger et al. | |
| 2007/0162124 A1 | 7/2007 | Whittaker | |
| 2008/0027430 A1 | 1/2008 | Montgomery et al. | |
| 2008/0161806 A1 | 7/2008 | Donnelly et al. | |
| 2008/0195204 A1 | 8/2008 | Zhukauskas et al. | |
| 2008/0234819 A1 | 9/2008 | Schmieding et al. | |

FOREIGN PATENT DOCUMENTS

| | | |
|---|---|---|
| WO | 8809157 A1 | 12/1988 |
| WO | 9818409 A1 | 5/1998 |
| WO | 0130253 A1 | 5/2001 |
| WO | 2005051205 A1 | 6/2005 |
| WO | 2007109769 A1 | 9/2007 |

OTHER PUBLICATIONS

Wu et al., Patterns of the Anteromedial and Posterolateral Grafts in a Double-Bundle Anterior Cruciate " Ligament Reconstruction", Journal of Orthopaedic Research, 2009, vol. 27, pgs. 879-884.
International Search Report, dated Jul. 2, 2010, pp. 1-6.

* cited by examiner

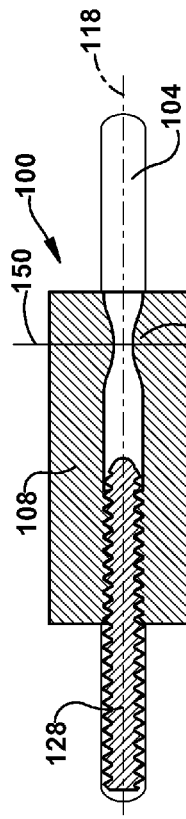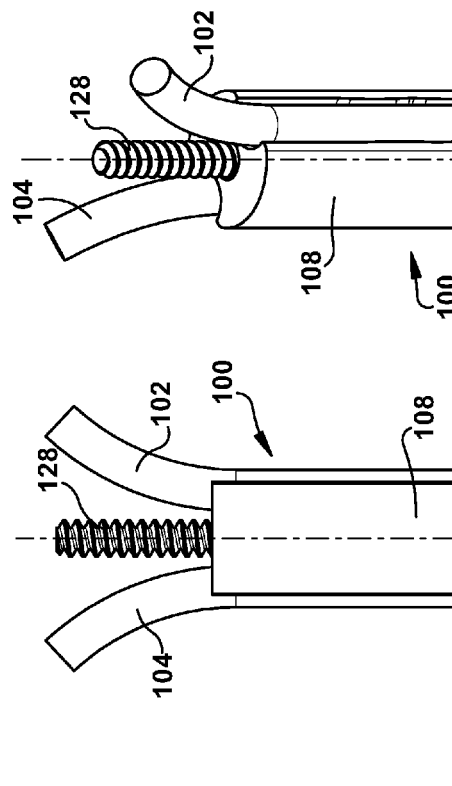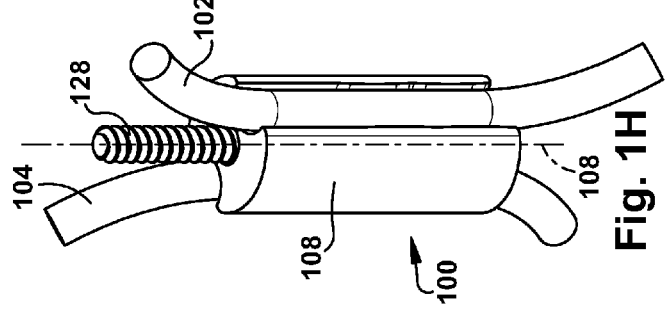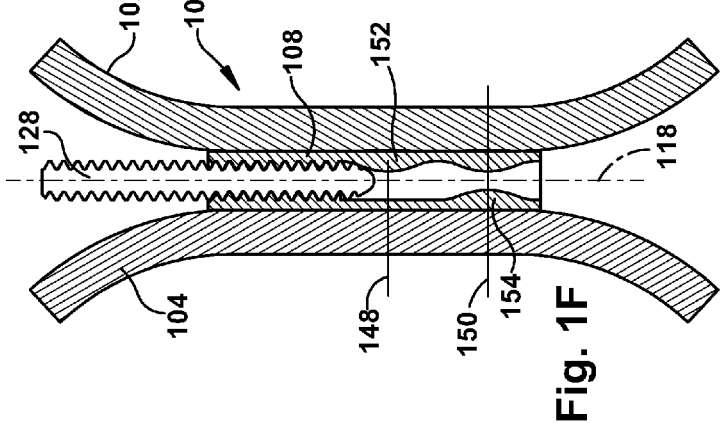

APPARATUS AND METHOD FOR SEQUENTIALLY ANCHORING MULTIPLE GRAFT LIGAMENTS IN A BONE TUNNEL

RELATED APPLICATION

This application is a continuation of U.S. patent application Ser. No. 12/765/444, filed 22 Apr. 2010, which claims priority from U.S. Provisional Application No. 61/171,518, filed Apr. 22, 2009, both of which are incorporated herein by reference in their entireties.

TECHNICAL FIELD

The present invention relates to an apparatus and method for anchoring graft ligaments and, more particularly, to an apparatus and method for sequentially anchoring multiple graft ligaments in a bone tunnel.

BACKGROUND OF THE INVENTION

Ligaments are tough bands of tissue which serve to connect the articular extremities of bones, or to support or retain organs in place within the body. Ligaments are typically composed of coarse bundles of dense fibrous tissue which are disposed in a parallel or closely interlaced manner, with the fibrous tissue being pliant and flexible, but not significantly extensible.

In many cases, ligaments are torn or ruptured as a result of trauma. As a result, various procedures have been developed to repair or replace such damaged ligaments.

For example, in the human knee, the anterior and posterior cruciate ligaments extend between the top end of the tibia and the bottom end of the femur. The anterior and posterior cruciate ligaments cooperate, together with other ligaments and soft tissue, to provide both static and dynamic stability to the knee. Often, the anterior cruciate ligament (hereafter, the "ACL") is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

In some circumstances, the graft ligament may be a ligament or tendon which is harvested from elsewhere in the patient (autograft) or from a cadaveric donor (allograft) (e.g., a hamstring); in other circumstances, the graft ligament may be a synthetic device. For the purposes of the following description, all of these types of ACL-replacing tissues will be collectively referred to as a "graft ligament".

The native ACL is not simply a band of connective tissue, but has a complex and partially twisted "double-bundle" structure in which an anteromedial portion/bundle of the ACL controls the forward-backward pivoting of the joint, and a posterolateral portion/bundle of the ACL controls rotational stability of the joint. When the knee is straight, these two bundles extend in a parallel manner between the femur and tibia. When the knee is flexed, the two bundles cross each other. The anteromedial and posterolateral bundles are subtly different in the manner in which they mechanically interact with each other and with other components of a healthy knee joint. For example, the anteromedial and posterolateral bundles may be under different amounts and/or directions of tensile force within the knee joint. It is common for patients with ACL injuries to have damage to both the anteromedial and posterolateral bundles.

Traditionally, a single graft ligament has been used to restore knee function to the patient by merely approximating the function of the native ACL. A single-graft technique involves drilling a single bone tunnel in each of the femur and tibia. This technique is well-established in the art and is considered a routine surgical procedure, after which patients typically return to their normal level of activity. However, a single-graft reconstruction does not reflect the original knee structure and therefore might lead to future adverse effects due to long-term use of the knee in a mechanically different configuration than the native anatomy.

In the last several years, surgeons have begun to refine their techniques to better mimic the double-bundle structure of the native ACL, as well, in the interest of creating a more "natural" replacement ACL and with the goal of a better long-term prognosis for achieving normal function of the reconstructed knee joint. One currently used double-bundle ACL replacement technique requires separate bone tunnels to be provided for each of the two reconstructive grafts. However, drilling two tunnels in close proximity is technically difficult and brings about a heightened risk of complication.

In a variation on this known technique, the two graft ligaments replacing the anteromedial and posterolateral bundles of the ACL both run from a single femoral bone tunnel to a single tibial bone tunnel. Due to the limited confines of the bone tunnels, traditional graft-anchoring techniques may not be effective in placing dual graft ligaments within a single tunnel. An example of a commercially available system which has been developed to address the specialized anchoring needs of a double-bundle ACL replacement is the AperFix™ system, available from Cayenne Medical of Scottsdale, Ariz. However, the AperFix™ product is limited in the manner in which each of the two graft ligaments can be manipulated (requiring a substantially symmetrical and simultaneous placement, tensioning, and anchoring of these two graft ligaments) and in aligning the bundles to replicate the placement of a native ACL within a single tunnel. Therefore, the graft ligaments used with currently available double- or single-tunnel systems do not, and cannot, accurately approximate the complex and individually varying mechanical interactions of the anteromedial and posterolateral bundles of a native ACL.

SUMMARY OF THE INVENTION

In an embodiment of the present invention, an apparatus for anchoring at least two graft ligaments within a longitudinal bone tunnel is described. A longitudinal sleeve has at least two radially spaced ligament-contacting surfaces located in lateral opposition to a sleeve inner lumen. The sleeve is configured for at least partial insertion into the bone tunnel with each graft ligament positioned laterally adjacent a different ligament-contacting surface. The graft ligaments are at least partially located between the bone tunnel and the sleeve. An actuating member has longitudinally separated proximal and distal actuating member ends. An asymmetrically offset profile is defined by at least one of the sleeve and the actuating member. The asymmetrically offset profile has a plurality of longitudinally spaced engagement thresholds. The actuating member is inserted longitudinally into the sleeve to cause frictional engagement of each graft ligament with both the bone tunnel and at least one ligament-contacting surface. The frictional engagement of each graft ligament is temporally spaced apart from the frictional engagement of at least one other graft ligament. The temporal spacing is provided by the plurality of engagement thresholds.

In an embodiment of the present invention, a method of anchoring at least two longitudinally extending graft ligaments within a bone tunnel during replacement of a native ACL is described. A first graft ligament is extended longitudinally through the bone tunnel. A second graft ligament is extended longitudinally through the bone tunnel at a location radially spaced apart from the first graft ligament. A sleeve is provided, the sleeve having a sleeve outer surface and longitudinally separated proximal and distal sleeve ends with a sleeve inner lumen extending therebetween. The sleeve is placed longitudinally within the bone tunnel with at least a portion of each of the first and second graft ligaments being located laterally between the sleeve outer surface and the bone tunnel. An actuating member is provided, the actuating member having an actuating member outer surface and longitudinally separated proximal and distal actuating member ends. An asymmetrically offset profile is defined in the longitudinal direction with at least one of the sleeve inner lumen and the actuating member outer surface. The asymmetrically offset profile defines longitudinally spaced first and second engagement thresholds. At least a portion of the actuating member is longitudinally inserted into the sleeve inner lumen. The actuating member is advanced distally into the sleeve inner lumen. A first predetermined tensile force is applied to the first graft ligament. The actuating member is advanced with respect to the sleeve, bringing at least a portion of both the actuating member and the sleeve laterally adjacent to the first engagement threshold to cause the first graft ligament to frictionally engage the sleeve outer surface and the bone tunnel. A second predetermined tensile force is applied to the second graft ligament. The actuating member is advanced with respect to the sleeve, bringing at least a portion of both the actuating member and the sleeve laterally adjacent to the second engagement threshold to cause the second graft ligament to frictionally engage the sleeve outer surface and the bone tunnel after the first graft ligament has frictionally engaged the sleeve outer surface and the bone tunnel.

In an embodiment of the present invention, a sequentially-actuated graft anchor system for use in anchoring at least two longitudinally extending graft ligaments within a bone tunnel during replacement of a native anterior cruciate ligament ("ACL") is described. A sleeve has a sleeve outer surface and longitudinally separated proximal and distal sleeve ends with a sleeve inner lumen extending therebetween. The sleeve defines a longitudinal axis, and the sleeve is adapted for longitudinal placement within the bone tunnel with at least a portion of the at least two graft ligaments being located laterally between the sleeve outer surface and the bone tunnel. An actuating member has an actuating member outer surface and longitudinally separated proximal and distal actuating member ends. At least a portion of the actuating member is adapted for selective longitudinal insertion into the sleeve inner lumen. At least one of the sleeve inner lumen and the actuating member outer surface defines an asymmetrically offset profile in the longitudinal direction. The asymmetrically offset profile has longitudinally spaced first and second engagement thresholds. Distal advancement of the actuating member into the sleeve inner lumen with respect to the sleeve, bringing at least a portion of both the actuating member and the sleeve laterally adjacent to the first engagement threshold causes a first one of the at least two graft ligaments to frictionally engage the sleeve outer surface and the bone tunnel before distal advancement of the actuating member into the sleeve inner lumen with respect to the sleeve, bringing at least a portion of both the actuating member and the sleeve laterally adjacent to the second engagement threshold causes a second one of the at least two graft ligaments to frictionally engage the sleeve outer surface and the bone tunnel.

BRIEF DESCRIPTION OF THE DRAWINGS

For a better understanding of the invention, reference may be made to the accompanying drawings, in which:

FIG. 1D is a top view of the embodiment of FIG. 1A;

FIG. 1E is a cross-section taken along line 1E-1E of FIG. 1D;

FIG. 1F is a cross-section taken along line 1F-1F of FIG. 1D;

FIG. 1G is a side view of the embodiment of FIG. 1D;

FIG. 1H is a perspective view of the embodiment of FIG. 1D;

DESCRIPTION OF EMBODIMENTS

Figure 3C:
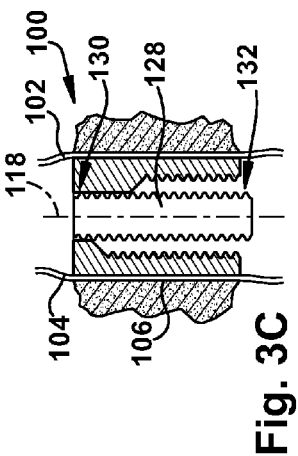
FIG. 3C is a cross-section taken along line 3C-3C of FIG. 3A.

In accordance with a first embodiment of the present invention, FIGS. 1A, 1B, 1C, 2A, 2B, 2C, 3A, 3B, and 3C schematically depict an apparatus 100 for anchoring at least two graft ligaments 102 and 104 within a longitudinal bone tunnel 106. More specifically, the apparatus 100 can be a sequentially-actuated graft anchor system 100 for use in anchoring at least two longitudinally extending graft ligaments 102 and 104 within a bone tunnel 106 during replacement of a native anterior cruciate ligament ("ACL"), and will be discussed as such herein. However, one of ordinary skill in the art will recognize that the apparatus 100 may be useful for sequentially anchoring any plurality of elongate strands within an aperture. For example, the apparatus 100 may be used to anchor a plurality of longitudinally extending graft ligaments within a bone tunnel during replacement of a native posterior cruciate ligament.

A longitudinal sleeve 108 has a sleeve outer surface 110 and longitudinally separated proximal and distal sleeve ends 112 and 114, respectively. (Element numbers are omitted from several of FIGS. 1A, 1B, 1C, 2A, 2B, 2C, 3A, 3B, and 3C for clarity of depiction.) A sleeve inner lumen 116 extends between the proximal and distal sleeve ends 112 and 114. The sleeve 108 defines a longitudinal axis 118. The sleeve 108 is adapted for longitudinal placement within the bone tunnel 106 with at least a portion of the at least two graft ligaments 102 and 104 located laterally (as shown by lateral direction arrow 120) between the sleeve outer surface 110 and the bone tunnel 106. The term "lateral" is used herein to reference a direction substantially perpendicular to the longitudinal axis 118.

Figure 2C:
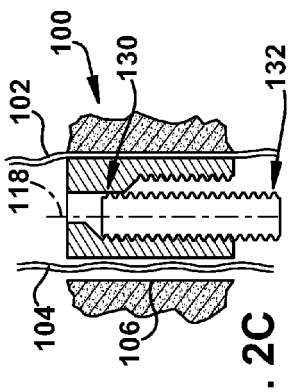
FIG. 2C is a cross-section taken along line 2C-2C of FIG. 2A.
Figure 1C:
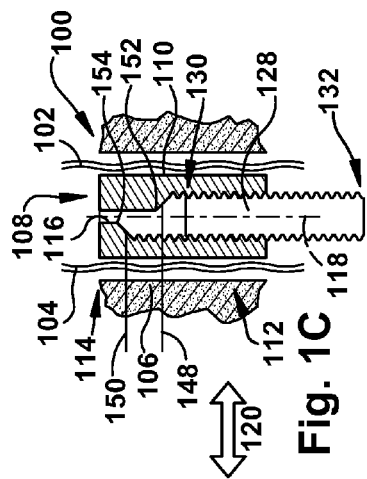
FIG. 1C is a cross-section taken along line 1C-1C of FIG. 1A.
Figure 3B:
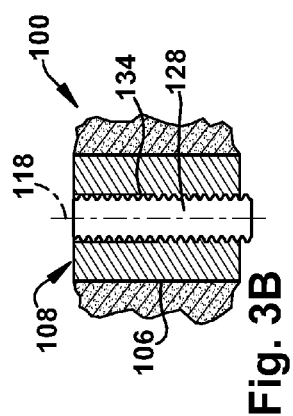
FIG. 3B is a cross-section taken along line 3B-3B of FIG. 3A.
Figure 2B:
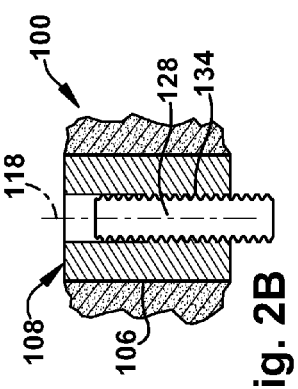
FIG. 2B is a cross-section taken along line 2B-2B of FIG. 2A.
Figure 1B:
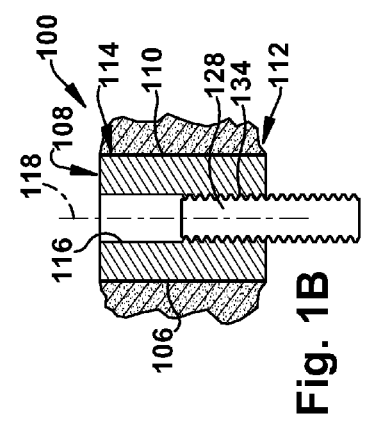
FIG. 1B is a cross-section taken along line 1B-1B of FIG. 1A.
Figure 3A:
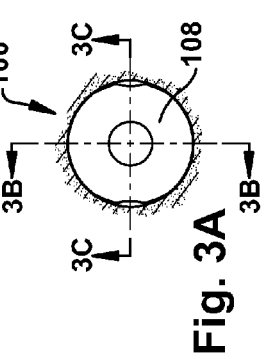
FIG. 3A is a schematic top view of the embodiment of FIG. 1A in a third condition.
Figure 2A:
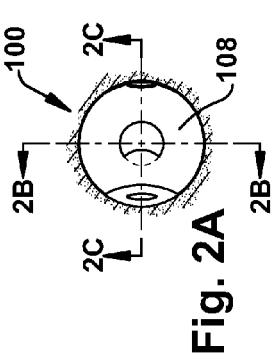
FIG. 2A is a schematic top view of the embodiment of FIG. 1A in a second condition.
Figure 1A:
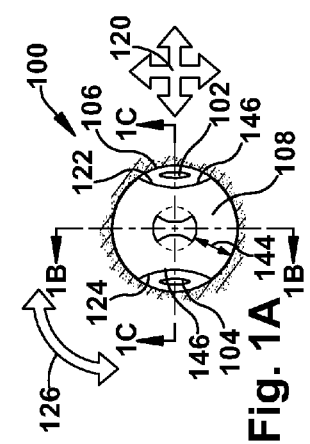
FIG. 1A is a schematic top view of an embodiment of the present invention in a first condition.

Optionally, and as shown in FIGS. 1A, 2A, and 3A, the sleeve 108 may include at least two radially spaced ligament-contacting surfaces, with first and second ligament-contacting surfaces 122 and 124, respectively, being spaced radially apart as shown by radial direction arrow 126. The term "radial" is used herein to reference a direction concentric to the longitudinal axis 118. The first and second ligament-contacting surfaces 122 and 124, when present, may be located on the sleeve 108 in lateral opposition to the sleeve inner lumen 116. The first and second ligament-contacting surfaces 122 and 124 may include texturization (e.g., grooves or dappling), adhesives, guide structures, different materials from other portions of the sleeve 108, or otherwise may be differentiated from remaining portions of the sleeve outer surface 110. In the depicted embodiment of FIGS. 1A, 2A, and 3A, each graft ligament 102 and 104 is positioned laterally adjacent a different one of the first and second ligament-contacting surfaces 122 and 124. The graft ligaments 102 and 104 thus are at least partially located between the bone tunnel 106 and the sleeve 108 when the sleeve is at least partially inserted into the bone tunnel 106. Regardless of whether a defined ligament-contacting surface is defined on a particularly discussed sleeve 108 herein, however, at least a portion of the sleeve outer surface 110 will be operative as described to contact the graft ligaments 102 and 104 as desired.

As shown in FIGS. 1B, 1C, 2B, 2C, 3B, and 3C, an actuating member 128 may be provided, the actuating member having longitudinally separated proximal and distal actuating member ends 130 and 132, respectively, and an actuating member outer surface 134. At least a portion of the actuating member may be adapted for selective longitudinal insertion into the sleeve inner lumen 116. At least one of the sleeve 108 and the actuating member 128 may have a cross-sectional footprint that is substantially at least one of circular, elliptical, curvilinear, and linear. The term "cross-sectional footprint" is used herein to indicate a silhouette or projection of all or a portion of the indicated structure, as taken in an orientation perpendicular to the longitudinal axis 118. FIGS. 1D, 1E, 1F, 1G, and 1H depict the apparatus 100 of FIG. 1A in three-dimensional form, with each of these Figures taken from a different vantage point.

Figure 4:
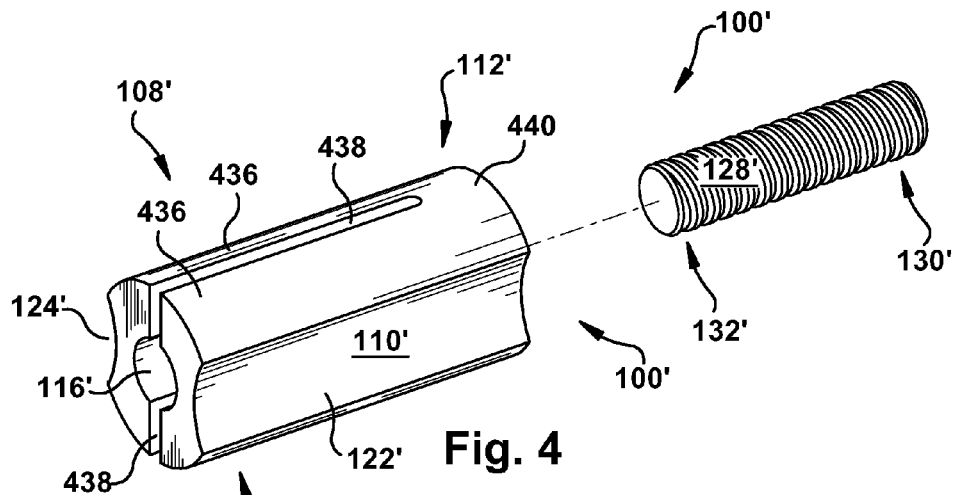
FIG. 4 is an exploded schematic view of an embodiment of the present invention.
Figure 5:
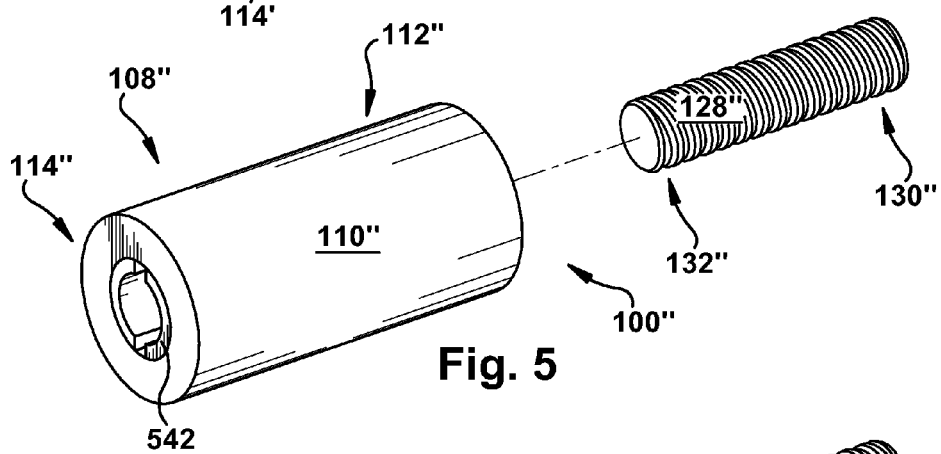
FIG. 5 is an exploded schematic view of an embodiment of the present invention.
Figure 6:
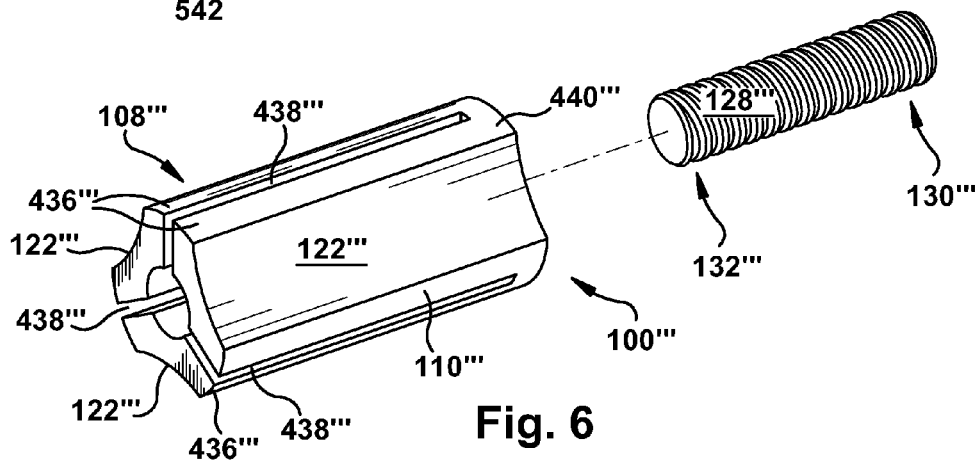
FIG. 6 is an exploded schematic view of an embodiment of the present invention.

FIGS. 4-6 depict exploded schematic views of several optional configurations of sleeve 108 and actuating member 128 pairs which could be used with the apparatus 100. For example, the sleeve 108' of FIG. 4 includes a plurality of longitudinally extending sleeve segment members 436, with each sleeve segment member including a portion of the sleeve outer surface 110' and defining a portion of the sleeve inner lumen 116'. Each of the sleeve segment members 436 can be configured to selectively frictionally engage a different graft ligament (not shown). This frictional engagement is optionally accomplished through the use of first and second ligament-contacting surfaces 122' and 124', which are laterally spaced from the sleeve inner lumen 116'. In the sleeve 108' of FIG. 4, the plurality of sleeve segment members 436 are spaced radially apart by at least one longitudinal aperture 438, and each of the sleeve segment members is connected to a sleeve aggregating member 440, here located at the proximal sleeve end 112', to form the sleeve 108'. As shown, the sleeve segment members 436 are formed integrally with the sleeve aggregating member 440, but the sleeve 108' could instead be constructed in any suitable manner from separately provided components. In use, the sleeve segment members 436 can flex relative to one another under proximal constraint by the sleeve aggregating member 440, the utility of which will become apparent below.

Optionally, the longitudinal apertures 438 may be at least partially filled with a flexible, resilient, elastically deformable, compressible, and/or expandable material to form an expansion joint (not shown). When a material is provided to connect adjacent sleeve segment members 436 and bridge across at least a portion of the intervening longitudinal aperture 438 via an expansion joint arrangement, the sleeve aggregating member 440 may be omitted from the sleeve 108' as being unnecessary to hold the sleeve segment members together.

The sleeve 108" of FIG. 5 is an example of a style which does not have specific ligament-contacting surfaces (though such could be provided in an alternate embodiment, not shown, of the sleeve of FIG. 5). Instead, because at least a portion of the outer sleeve surface 110" reflects the shape of the bone tunnel (not shown, but presumed here to be cylindrical), the graft ligaments may be placed in any relationship to the outer sleeve surface 110" which will facilitate the desired anchoring. In the embodiment of FIG. 5, the outer sleeve surface 110" is configured to provide a cylindrical aspect to the sleeve 108" corresponding to that of the presumed bone tunnel. Because the depicted sleeve 108" does not include longitudinal apertures or other means for facilitating lateral expansion, the sleeve of FIG. 5 may be made of a flexible and optionally resilient, compressible, and/or elastically deformable material, such as, but not limited to, a rubber or plastic material of any suitable type. Optionally, an inner lumen liner 542 of a more-rigid material may be provided to facilitate transfer of forces between the actuating member 128" and the outer sleeve surface 110", as discussed below.

FIG. 6 depicts a sleeve 108'" which is similar to that of FIG. 4 but includes an additional sleeve segment member 436". In the FIG. 6 embodiment, the structure and function are similar to those described for the FIG. 4 embodiment, which will not be repeated here, but three ligament-contacting surfaces (all labeled 122'" for clarity) are available for use. Any number of the ligament-contacting surfaces can be used to anchor a suitable number of graft ligaments in the manner described below, and the number of ligament-contacting surfaces for any embodiment of the present invention is not necessarily equal to the number of graft ligaments being anchored.

While FIGS. 4-6 depict examples of apparatuses 100', 100", and 100'" which include various combinations of features and structures, there is no limit placed on the number, type, structure, or any other characteristics of the elements which may be combined for use in the present invention. Additionally, each ligament-contacting surface in any embodiment of the present invention may be used to anchor zero, one, or more than one graft ligament during use of that embodiment.

With reference once again, to FIGS. 1A, 1B, 1C, 2A, 2B, 2C, 3A, 3B, and 3C, and regardless of the specific structure or design of the apparatus 100, a sleeve thickness 144 may be defined between the sleeve outer surface 110 and the sleeve inner lumen 116. The sleeve thickness 144 corresponds to a laterally measured amount of sleeve 108 material and may be taken at any point radially around the circumference of the sleeve or longitudinally along the length of the sleeve. Each graft ligament 122 and 124 may be located laterally adjacent at least a portion of a graft ligament position 146 defined on the sleeve outer surface 110, with the graft ligament positions 146 being optionally associated with one or more ligament-contacting surfaces 122 and 124, when present. The sleeve thickness 144 may be a minimum sleeve thickness (disregarding any longitudinal apertures or other localized voids on the sleeve 108) at the graft ligament positions 146. The sleeve thickness 144 may also or instead be a maximum sleeve thickness at a location substantially radially equidistant from each of the graft ligament positions 146. Thus, the sleeve thickness 144 may be used by one of ordinary skill in the art as a tool to quantify and design a sleeve 108 having desired thickness properties for a particular application of the present invention.

At least one of the sleeve 108 and the actuating member 128 may define an asymmetrically offset profile, the asymmetrically offset profile being located at the sleeve-actuating member interface and having a plurality of longitudinally spaced engagement thresholds. The phrase "asymmetrically offset" is used herein to indicate an arrangement wherein a plurality of abrupt changes in the profile of the "offset" structure are located on opposite sides of a dividing line or median plane, or about a center or axis, without a correspondence in relative position. For example, and returning to FIGS. 1A, 1B, 1C, 2A, 2B, 2C, 3A, 3B, and 3C, at least one of the sleeve inner lumen 116 and the actuating member outer surface 134 may define the asymmetrically offset profile in the longitudinal direction, with the asymmetrically offset profile having longitudinally spaced first and second engagement thresholds 148 and 150, respectively. It is contemplated that the asymmetrically offset profile is not necessarily asymmetrical in every conceivable orientation, but that the asymmetry in a particular orientation of interest, such as those shown in the Figures, is sufficient to create the effects and functions described herein.

As is shown in at least FIGS. 1C, 2C, and 3C, the asymmetrically offset profile may include at least one shoulder (two shoulders 152 and 154 shown) defining at least one of the first and second engagement thresholds 148 and 150. The shoulder(s) 152 and 154, when present, are located on a chosen one of the sleeve inner lumen 116 and the actuating member outer surface 134. The shoulder(s) 152 and 154 then interact with the other one of the sleeve inner lumen 116 and the actuating member outer surface 134 to move the sleeve outer surface 110 laterally outward and into frictional engagement with at least one graft ligament 102 and 104. This interaction is prompted and/or caused by relative movement of the actuating member 128 and the sleeve 108, as discussed in detail below. The shoulder(s) 152 and 154 may be angular, curved, curvilinear, or any other shape and may be formed on the chosen one of the sleeve inner lumen 116 and the actuating member outer surface 134 in any suitable manner.

The embodiment of the present invention shown in FIGS. 1A-3C has an asymmetrically offset profile defined by the sleeve inner lumen 116. The first engagement threshold 148 is defined by a first shoulder 152 extending laterally inward toward the longitudinal axis 118 at a first radial location, and the second engagement threshold 150 is defined by a second shoulder 154 extending laterally inward toward the longitudinal axis, optionally at a second radial location. The second radial location, when present, is longitudinally and radially spaced from the first radial location, as is readily apparent from at least FIG. 1C. Optionally, and as is the case with the embodiment of FIGS. 1A-3C, the second radial location may be located radially opposite the first radial location about a circumference of the sleeve 108. However, the first and second radial locations will generally bear a direct relationship to the desired placement of the graft ligaments 102 and 104 about a circumference (when curvilinear) or other inner perimeter shape of the bone tunnel 106. It is contemplated that additional shoulders (not shown) corresponding to additional engagement thresholds (not shown) may be present when more than two graft ligaments are to be anchored, and, depending upon the planned securement, the second shoulder 154 could serve to reinforce the anchoring provided by the first shoulder 152. For example, and as shown in FIG. 1E, the second shoulder 154 could extend around a substantial portion of the sleeve inner lumen 116. One of ordinary skill in the art can readily provide an asymmetrically offset profile to at least one of the sleeve inner lumen 116 and actuating member outer surface 134 which will anchor the graft ligaments in the desired sequence.

The sleeve 108 depicted in FIGS. 1A-3C is an elastomeric or otherwise at least partially resilient sleeve which allows the material of the sleeve to be compressed by the actuating member 128 such that the sleeve expands laterally to frictionally engage the graft ligaments 102 and 104 without a corresponding lateral contraction elsewhere around the sleeve circumference (especially shown in FIGS. 1A, 2A, and 3A). However, the sleeve 108, actuating member 128, or any other structures of the present invention could be made of any suitable material or combination of material having desired properties for a particular application of the present invention.

Optionally, and as discussed above with reference to FIG. 5, a one-piece or multiple-piece inner lumen liner (not shown in FIGS. 1A-3C) may be located in the sleeve inner lumen 116 to facilitate force transfer between the actuating member 128 and sleeve 108.

In the embodiment of FIGS. 1A-3C, a substantially straight-sided actuating member 128 interacts with an asymmetrically offset profile on the sleeve inner lumen 116. In contrast, FIGS. 7A-9B schematically depict an apparatus 100b according to a second embodiment of the present invention.

Figure 7A:
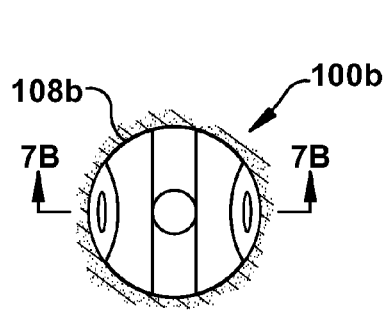
FIG. 7A is a schematic top view of an embodiment of the present invention in a first condition.
Figure 7B:
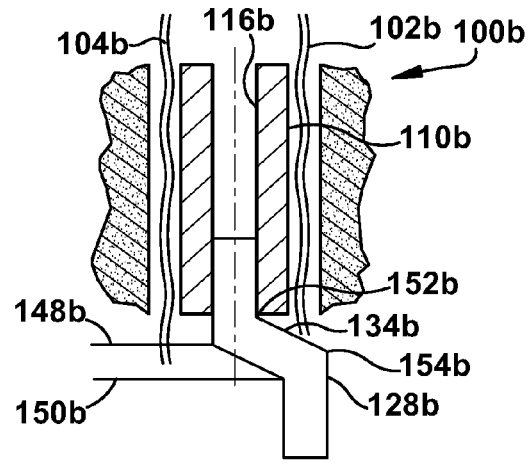
FIG. 7B is a cross-section taken along line 7B-7B of FIG. 7A.
Figure 8A:
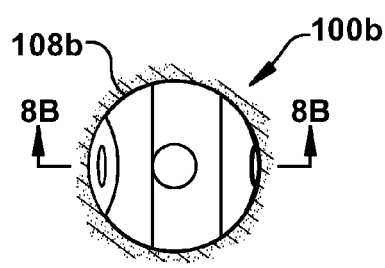
FIG. 8A is a schematic top view of the embodiment of FIG. 7A in a second condition.
Figure 8B:
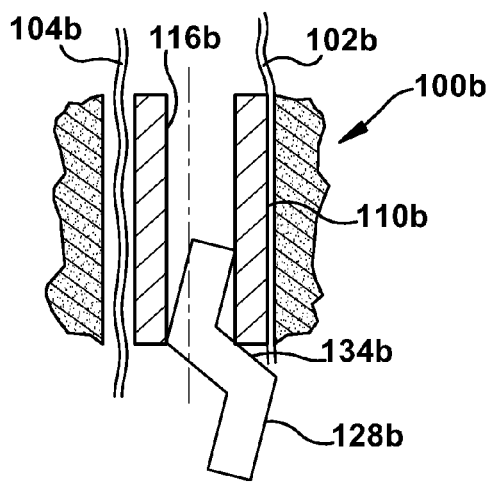
FIG. 8B is a cross-section taken along line 8B-8B of FIG. 8A.
Figure 9A:
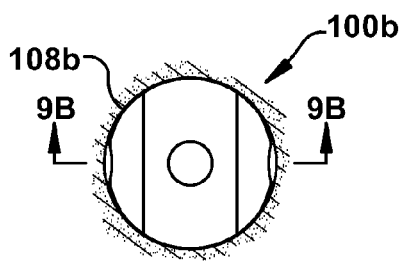
FIG. 9A is a schematic top view of the embodiment of FIG. 7A in a third condition.
Figure 9B:
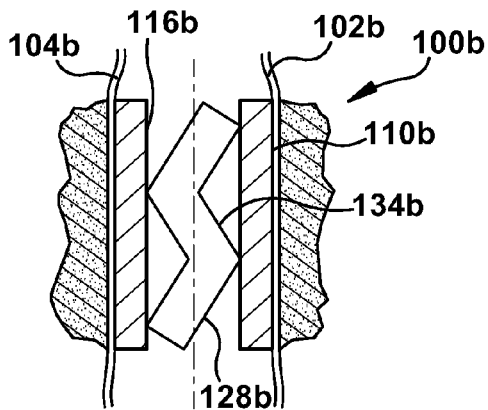
FIG. 9B is a cross-section taken along line 9B-9B of FIG. 9A.

The apparatus 100b of FIGS. 7A-9B is similar to the apparatus 100 of FIGS. 1A-3C and therefore, structures of FIGS. 7A-9B that are the same as or similar to those described with reference to FIGS. 1A-3C have the same reference numbers with the addition of the suffix "a". Description of common elements and operation similar to those in the previously described first embodiment will not be repeated with respect to the second embodiment. In the embodiment of FIGS. 7A-9B, the sleeve 108 is more rigid than in the previously described embodiment and the asymmetrically offset profile is on the actuating member outer surface 134b. Accordingly, the first and second engagement thresholds 148b and 150b are defined by first and second shoulders 152b and 154b on the actuating member 128b. Interaction between the actuating member 128b and the sleeve 108 pushes the sleeve outer surface 110b laterally outward and into frictional engagement with the graft ligaments 102b and 104b in a similar manner to that described below with reference to the first embodiment. While the sleeve 108 in the top views of FIGS. 7A, 8A, and 9A is depicted as having a lateral gap between two opposed ligament-contacting sides, it is contemplated that a flexible sheath, sleeve aggregating member, or other unifying structure (not shown) could be provided to facilitate handling and installation of the depicted sleeve.

The first embodiment of FIGS. 1A-3C is used here to illustrate a described method of anchoring at least two longitudinally extending graft ligaments 102 and 104 within a bone tunnel 106, with replacement of a native ACL being the example application for the method. To prepare for the anchoring and bring the apparatus 100 into the arrangement of FIGS. 1A-1C, the first graft ligament 102 is extended longitudinally through the bone tunnel 106, and the second graft ligament 104 is extended longitudinally through the bone tunnel at a location radially spaced from the first graft ligament. The sleeve 108 is placed longitudinally within the bone tunnel 106 with at least a portion of each of the first and second graft ligaments 102 and 104 being located laterally between the sleeve outer surface 110 and the bone tunnel. Optionally, the first and second graft ligaments 102 and 104 may respectively be located laterally between first and second ligament-contacting surfaces 122 and 124 and the bone tunnel 106.

Once the graft ligaments 102 and 104 and sleeve 108 are arranged within the bone tunnel 106, at least a portion of the actuating member 128 is longitudinally inserted into the sleeve inner lumen 116. The actuating member 128 is then advanced distally into the sleeve inner lumen 116, with respect to the sleeve 108, in any suitable manner. For example, the actuating member 128 may threadably engage with the sleeve inner lumen 116, as shown in FIGS. 1A-3C, to produce the claimed distal advancement of the actuating member into the sleeve inner lumen. As another example, the actuating member 128b may slidably engage with the sleeve inner lumen 116b, as shown in FIGS. 7A-9B, to produce the claimed distal advancement.

Regardless of the way in which the actuating member 128 is advanced distally into the sleeve inner lumen 116, the user applies a first predetermined force, which will normally be a tensile force, to the first graft ligament 102 before anchoring. In an ACL replacement procedure, this force may correspond to the force exerted on/by the first bundle of a native ACL. Once the first graft ligament 102 has been adjusted as desired, the actuating member 128 is advanced distally across the first engagement threshold 148 to cause the first graft ligament to frictionally engage the sleeve outer surface 110 and the bone tunnel 106. More particularly, in the embodiment of FIGS. 1A-3C, as the actuating member 128 reaches the first engagement threshold 148, at least a portion of both the actuating member and the sleeve 108 become laterally adjacent to the first engagement threshold 148. In this arrangement, the distal actuating member end 132 presses against the first shoulder 152 and thus presses at least a local portion of the sleeve 108 outward to engage the first graft ligament 102 as described. At this point the apparatus 100 is in substantially the position depicted schematically in FIGS. 2A-2C, with the first graft ligament 102 anchored.

The actuating member 128 is then advanced further distally in any suitable manner and the body of the actuating member partially blocks the sleeve inner lumen 116 and thus prevents the laterally expanded portion of the sleeve 108 (i.e., the portion pressed laterally outward toward the first graft ligament 102) from reverting to an original position. At any time before, during, or after the first graft ligament 102 is anchored, the user applies a second predetermined force, which will normally be a tensile force, to the second graft ligament 104 before anchoring. In an ACL replacement procedure, this force may correspond to the force exerted on/by the second bundle of a native ACL. Once the second graft ligament 104 has been adjusted as desired, the actuating member 128 is advanced distally across the second engagement threshold 150 to cause the second graft ligament to frictionally engage the sleeve outer surface 110 and the bone tunnel 106. More particularly, in the embodiment of FIGS. 1A-3C, as the actuating member 128 reaches the second engagement threshold 150, at least a portion of both the actuating member and the sleeve 108 become laterally adjacent to the second engagement threshold 150. In this arrangement, the distal actuating member end 132 presses against the second shoulder 154 and thus presses at least a local portion of the sleeve 108 outward to engage the second graft ligament 104 as described. At this point the apparatus 100 is in substantially the position depicted schematically in FIGS. 3A-3C, with the first and second graft ligaments 102 and 104 anchored.

It should be noted that the frictional engagement of each of the first and second graft ligaments 102 and 104, and indeed of any other provided graft ligaments (not shown), with both the bone tunnel 106 and the sleeve 108 (optionally at a ligament-contacting surface) is temporally spaced apart from the frictional engagement of at least one other graft ligament with the bone tunnel 106 and the sleeve 108. This temporal spacing is provided by the engagement thresholds associated with each of the graft ligaments, and can be controlled by one of ordinary skill in the art through placement and design of the engagement thresholds.

Optionally, and as shown in FIGS. 1A-3C, the actuating member 128 may advance substantially laterally symmetrically along the longitudinal axis 118 concurrently with lateral movement of at least a portion of the sleeve 108 away from the longitudinal axis as the actuating member crosses the first and second engagement thresholds 148 and 150 while traveling in the distal direction. In other words, the actuating member 128 is advanced (e.g., via the threaded engagement of FIGS. 1A-3C) in a manner which appears linear from the frame of reference of the bone tunnel and pushes various portions of the sleeve 108 successively outward through engagement of the distal actuating member end 132 with the first and second shoulders 152 and 154. This situation is most likely to occur when the asymmetrically offset profile is on the sleeve inner lumen 116, as opposed to the actuating member outer surface 134, and may be facilitated by the choice of a sleeve 108 material which has the desired rigidity and compressibility properties to accomplish the anchoring in a suitable manner.

While the above description uses the first embodiment of FIGS. 1A-3C as an example, one of ordinary skill in the art can readily translate the described events to an embodiment, such as the second embodiment shown in FIGS. 7A-9B, having the asymmetrically offset profile located on the actuating member 128. In this latter configuration, the temporal spacing of the anchoring of the first and second graft members 102 and 104 is also provided by the engagement thresholds; the engagement thresholds are merely located on a different portion of the apparatus 100 than in the first embodiment of FIGS. 1A-3C.

In configurations of the sleeve 108 including sleeve segment members 436, such as those of FIGS. 4 and 6, the first and second (and any additionally provided) shoulders 152 and 154 may each be associated with a sleeve segment member. During deployment of apparatuses having these or similar configurations, the actuating member 128 may flex the sleeve segment members 436 outward and into frictional engagement with associated graft ligaments 102 and 104 through pressure of the distal actuating member end 132 on the first and second shoulders 152 and 154.

Though the above description refers to the sleeve 108 as being "expanded" into contact with the first and second graft ligaments 102 and 104, one of ordinary skill in the art will recognize that various radially spaced portions of the sleeve may be laterally moved and/or shifted into engagement with the first and second graft ligaments and/or the bone tunnel in various ways, depending upon the material and structure of the sleeve, and the interrelations of the asymmetrically offset profile with the other portions of the apparatus 100. The sleeve 108 may be a unitary piece or may be formed of separate component parts. One of ordinary skill in the art will also be readily able to provide an elastically or plastically deformable sleeve 108 and control the interaction of various portions of the apparatus 100 to anchor the first and second graft ligaments 102 and 104 accordingly.

While aspects of the present invention have been particularly shown and described with reference to the preferred embodiment above, it will be understood by those of ordinary skill in the art that various additional embodiments may be contemplated without departing from the spirit and scope of the present invention. For example, the specific method described above for installing the apparatus 100 is merely illustrative; one of ordinary skill in the art could readily determine any number of tools, sequences of steps, or other means/options for placing the apparatus, or components thereof, into positions substantively similar to those shown and described herein. Any of the described structures and components could be integrally formed or separately provided of any suitable material or combinations of materials; however, the chosen material(s) should be biocompatible for most applications of the present invention. Though certain components described herein are shown as having specific geometric shapes (e.g., the cylindrical sleeve 108" and actuating member 128" of the FIG. 5 embodiment), all structures of the present invention may have any suitable shapes, sizes, configurations, relative relationships, cross-sectional areas, or any other physical characteristics as desirable for a particular application of the present invention. The apparatus 100 could be configured to collapse and deploy in any suitable manner. The apparatus 100 could have a structure, or portions thereof, with inflation/expansion, pliability, rigidity, solidity, hollowness, or any other physical properties as desired for a particular application of the present invention. The apparatus 100 may be placed at the anchoring site in any suitable manner; for example, portions of the apparatus could be placed via open surgery and/or advanced through a previously installed sheath, trocar, or tube which terminates near the anchoring site. The inner lumen liner 542, when present, may be shaped to include the asymmetrically offset profile and transfer forces from the actuating member 128 to the sleeve outer surface 110 to anchor a plurality of graft ligaments. A description of a "circumference" or "radial" direction with reference to a curvilinear structure should be interpreted as meaning an analogous feature or direction for a structure which includes non-curvilinear portions. When there are more than two graft ligaments to be anchored, the asymmetrically offset profile may include some symmetries which allow more than one, but not all, of the graft ligaments to be frictionally engaged at substantially the same time. Any portion of the sleeve outer surface 110 may conform to the shape of the adjacent bone tunnel 106 to any degree, during any stage of the deployment and use of the apparatus 100, as desired by the user, and the material of the sleeve 108 may be chosen to create a desired degree of conformation. At least a portion of the actuating member 128 may be longitudinally inserted into the sleeve inner lumen 116 at any time before, while, or after the graft ligaments 102 and 104 and sleeve 108 are arranged within the bone tunnel 106. An external tool or structure (not shown) may be used to manipulate and/or steady one or both of the sleeve 108 and actuating member 128 during use. Sleeve aggregating members 440 could be located at either or both of the proximal and distal sleeve ends 112 and 114 for an apparatus 100 having a plurality of sleeve segment members 436. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for anchoring at least two elongate strands within a longitudinal bone tunnel, the apparatus comprising:
    a longitudinal sleeve having an internal surface defining a lumen and an external surface having at least two radially spaced strand-contacting surfaces thereon, the sleeve being configured for at least partial insertion into the bone tunnel with each elongate strand positioned laterally adjacent respective ones of said strand-contacting surfaces, with each of the elongate strands being at least partially located between the bone tunnel and the sleeve;
    an actuating member having a longitudinal axis and longitudinally separated and axially misaligned proximal and distal actuating member ends and being substantially rotationally symmetrical about the longitudinal axis;
    an asymmetrically offset profile defined by the sleeve and oriented substantially parallel to the longitudinal axis, the asymmetrically offset profile defining a plurality of longitudinally spaced engagement thresholds;
    wherein when the actuating member is inserted longitudinally into the sleeve it causes frictional engagement of each elongate strand with both the bone tunnel and at least one of said strand-contacting surfaces, the frictional engagement of each elongate strand located between the bone tunnel and the sleeve being temporally spaced apart from the frictional engagement of at least one other elongate strand located between the bone tunnel and the sleeve, the temporal spacing being provided by the longitudinal spacing of the plurality of engagement thresholds.

2. The apparatus of claim 1, wherein the plurality of engagement thresholds includes first and second engagement thresholds,
    wherein the first engagement threshold is defined by a first shoulder of the sleeve extending laterally inward toward the longitudinal axis at a first radial location to define at least a portion of the asymmetrically offset profile, and the second engagement threshold is defined by a second shoulder of the sleeve extending laterally inward toward the longitudinal axis at a second radial location to define at least a portion of the asymmetrically offset profile, the second radial location being longitudinally and radially spaced apart from the first radial location.

3. The apparatus of claim 1, wherein the plurality of engagement thresholds includes first and second engagement thresholds,
wherein when the actuating member advances laterally symmetrically along the longitudinal axis concurrently with lateral movement of at least one of said strand-contacting surfaces away from the longitudinal axis, the actuating member successively advances across said first and second engagement thresholds in a distal direction to actuate operation of at least a portion of the apparatus.

4. The apparatus of claim 1, wherein relative distal advancement of the distal actuating member end with respect to the sleeve brings at least a portion of both the actuating member and the sleeve laterally adjacent to a first engagement threshold of the plurality of engagement thresholds, and causes a first one of said at least two elongate strands to frictionally engage a respective one of said strand-contacting surfaces and the bone tunnel before distal advancement of the distal actuating member end brings a portion of both the actuating member and the sleeve laterally adjacent to a second engagement threshold of the plurality of engagement thresholds, which causes a second one of said at least two elongate strands to frictionally engage the respective one of said strand-contacting surface and the bone tunnel.

5. The apparatus of claim 1, wherein said at least two strand-contacting surfaces include first and second strand-contacting surfaces, the first and second strand-contacting surfaces being spaced radially apart by at least one longitudinal aperture, and wherein each of the first and second strand-contacting surfaces is connected to a sleeve aggregating member to at least partially form the sleeve.

6. The apparatus of claim 1, wherein the plurality of engagement thresholds includes first and second engagement thresholds,
wherein the first and second engagement thresholds define the asymmetrically offset profile,
the first and second engagement thresholds each including one shoulder located on the sleeve, wherein the shoulder interacts with the actuating member to move one of said strand-contacting surfaces laterally outward and into frictional engagement with at least one elongate strand when the sleeve and the actuating member become located laterally adjacent to a respective one of said first and second engagement thresholds.

7. The apparatus of claim 1, wherein the actuating member engages with the internal surface of the sleeve to produce distal advancement of the actuating member into the sleeve lumen.

8. The apparatus of claim 1, wherein a sleeve thickness is defined between the sleeve outer surface and the sleeve internal surface, and wherein the elongate strands are positioned laterally adjacent respective ones of said strand-contacting surfaces at an elongate strand position, so that the sleeve thickness is a minimum sleeve thickness at the elongate strand positions and is a maximum sleeve thickness at a location substantially radially equidistant from each of the elongate strand positions.

9. The apparatus of claim 1, wherein at least one of the sleeve and the actuating member has a cross-sectional footprint that is substantially at least one of circular, elliptical, curvilinear, and linear.

10. The apparatus of claim 1, wherein the apparatus is a sequentially-actuated graft anchor system for use in anchoring at least two longitudinally extending ones of the at least two elongate strands within the bone tunnel during replacement of a strand.

11. The apparatus of claim 10, wherein the elongate strand is a native anterior cruciate ligament ("ACL").

12. The apparatus of claim 1, wherein the plurality of engagement thresholds includes first and second engagement thresholds and the at least two radially spaced strand-contacting surfaces includes a first strand-contacting surface and a second strand-contacting surface,
wherein the asymmetrically offset profile includes a first shoulder, located on the sleeve, that defines the first engagement threshold, the first engagement threshold corresponding to the first strand-contacting surface,
and a second shoulder, located on the sleeve, that defines the second engagement threshold, the second engagement threshold corresponding to the second strand-contacting surface;
wherein when the actuating member is inserted longitudinally into the sleeve into a position laterally adjacent the first engagement threshold, the first shoulder exerts pressure upon the actuating member to cause the first strand-contacting surface to move laterally outward from the longitudinal axis while the second strand-contacting surface remains substantially stationary with respect to the longitudinal axis;
and wherein when the actuating member is inserted longitudinally into the sleeve into a position simultaneously laterally adjacent the first and second engagement thresholds, the first shoulder exerts pressure upon the actuating member to cause the first strand-contacting surface to move laterally outward from the longitudinal axis and the second shoulder exerts pressure upon the actuating member to cause the second strand-contacting surface to move laterally outward from the longitudinal axis.

13. The apparatus of claim 12, wherein before, during, and after longitudinal insertion of the actuating member into the sleeve, each of said elongate strands is able to be simultaneously located laterally adjacent a respective one of said strand-contacting surfaces.

14. The apparatus of claim 1, wherein the asymmetrically offset profile is located at an interface of the sleeve and the actuating member.

* * * * *